United States Patent [19]

Russell et al.

[11] Patent Number: 5,717,047
[45] Date of Patent: Feb. 10, 1998

[54] MATERIALS

[75] Inventors: Jeremy Colin Russell, Middlesex; Stephen Alexander Charles, Oxon; Richard Neil Templar Freeman; Judith Elizabeth Browne, both of Middlesex, all of United Kingdom

[73] Assignee: Biocompatibles Limited, Middlesex, United Kingdom

[21] Appl. No.: 464,692

[22] PCT Filed: Jan. 28, 1994

[86] PCT No.: PCT/GB94/00177
  § 371 Date: Jun. 7, 1995
  § 102(e) Date: Jun. 7, 1995

[87] PCT Pub. No.: WO94/16748
  PCT Pub. Date: Aug. 4, 1994

[30] Foreign Application Priority Data

Jan. 28, 1993 [GB] United Kingdom ............... 9301702

[51] Int. Cl.$^6$ ............... C08F 130/02; C08F 128/02; C08F 120/56; C08F 120/18; C08F 116/12; C08F 112/08

[52] U.S. Cl. ............... 526/278; 526/287; 526/310; 526/303.1; 526/328; 526/346; 526/332

[58] Field of Search ............... 526/278, 287, 526/303.1, 310, 328, 332, 346

[56] References Cited

U.S. PATENT DOCUMENTS

| | | | |
|---|---|---|---|
| 4,610,979 | 9/1986 | Lautenschlager et al. | 514/77 |
| 5,066,745 | 11/1991 | Engelhardt et al. | 526/240 |

FOREIGN PATENT DOCUMENTS

| | | | |
|---|---|---|---|
| 0 161 759 | 11/1985 | European Pat. Off. | A61K 9/50 |
| 0 251 229 | 1/1988 | European Pat. Off. | C07F 9/10 |
| WO 86/02933 | 5/1986 | WIPO | C08G 18/38 |
| WO 87/02684 | 5/1987 | WIPO | C08K 5/00 |
| WO 88/00956 | 2/1988 | WIPO | C08G 63/68 |
| WO 92/06719 | 4/1992 | WIPO | A61L 33/00 |
| WO 92/07885 | 5/1992 | WIPO | C08F 212/14 |
| WO 93/01221 | 1/1993 | WIPO | C08F 246/00 |
| WO 93/05081 | 3/1993 | WIPO | C08F 8/40 |

OTHER PUBLICATIONS

*Chemistry and Physics of Lipis* 16 (1976) 107–114, A P J Mank et al.

Platelet Activating Factor—INSERM Symposium No. 23 eds Benvenieste J and Arnoux B, (1983) pp. 49–56, et al.

*Primary Examiner*—Joseph L. Schofer
*Assistant Examiner*—Wu C. Cheng
*Attorney, Agent, or Firm*—Sughrue, Mion, Zinn, Macpeak & Seas, PLLC

[57] ABSTRACT

The present invention relates to materials which comprise a surface having pendant groups of formula (I), in which the groups —B— are the same or different, preferably the same, and each is —$CH_2$— or —C(=O)—, preferably —$CH_2$—, $R^1$ is hydrogen alkyl of 1 to 12, preferably 1 to 4 carbon atoms, or a group capable of bonding to, or bonded to, a ligand or $R^1$ is a polymerisable, preferably ethylenically unsaturated, group and Z is a zwitterionic group. Usually both groups B are the same and are joined to identical groups so that the compound of formula (I) is achiral. New compounds are achiral glyceryl phosphatidyl choline analogues. Surfaces having the groups (I) at their surface have improved biocompatibility, and show reduced fibrinogen absorption, reduced platelet activation, reduced microorganism adhesion and are useful in the production of implants or prostheses, for extra-corporeal circuitry for body fluids, for treating membranes of various type, for contact lenses. The compounds may also be used to form liposomes.

21 Claims, No Drawings

MATERIALS

The present invention relates to new materials which comprise a surface having pendent zwitterionic groups processes for producing the materials, the use of compounds to provide such a material and to improve biocompatibility and to a device having such a surface. It also relates to new compounds useful in providing such materials.

Our earlier patent applications WO-A-92/06719, EP-A-32622 and WO-A-92/21386 disclose that natural and synthetic phospholipids coated on a surface show improved biocompatibility and in particular haemocompatibility compared to an untreated surface. Thus, materials coated with such phospholipids are proposed as suitable for use in applications where they come into contact with body fluids, such as blood, or protein-containing fluids generally, so as to reduce protein adsorption and/or reduce activation of blood platelets. These materials may therefore be used to treat devices to be implanted into the body or apparatus or which comes into contact with such fluids extra-corporeally such as separation apparatus and in particular separation membranes. Such compounds may also be used to form liposomes as described in EP-A-32622 and EP-A-161759, which may for example be used to administer substances encapsulated within them.

The compounds disclosed in the above applications are phospholipids which comprise a glycerol-type structure as shown below:

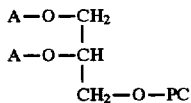

in which the two groups A are long-chain acyl groups and PC is a phosphoryl choline group or analogue thereof.

The compounds however possess a chiral carbon atom which can render them difficult to purify. In addition, the etheric oxygen linkages to the groups A are derived from primary and secondary alcohol groups. The difference in the reactivity of these two hydroxyl groups can lead to problems in the efficient preparation of the compounds.

Other glycerophosphatidyl choline (GPC) derivatives have also been used in a number of techniques for producing biocompatible articles, for instance, WO-A-86/02933 and WO-A-88/00956 disclose polyurethanes and polyesters respectively obtainable by copolymerisation using a GPC derivative as one of the comonomers. Other such polymerisable derivatives have been disclosed in WO-A-92/07885, which discloses crosslinked copolymers of such derivatives suitable for use in making contact lenses, WO-A-93/01221 which discloses copolymers of such derivatives, suitable for use as surface treatments, and our unpublished application PCT/GB92/01580 which discloses graft polymers of such derivatives suitable for use as surface treatments. In addition, WO-A-91/13639 discloses the treatment of a surface with an activated derivative of GPC, so as to bind covalently to the surface. Finally, WO-A-87/0284 discloses the use of GPC derivatives an additive for thermopolymers which render the polymers biocompatible.

We have also found that compounds containing phosphoryl choline groups can also reduce the adhesion or growth of microorganisms such as bacteria, yeast, algae and fungi, and in particular bacteria at a surface. This renders the use of compounds containing such groups advantageous in a variety of situations where the growth of such microorganisms is undesirable.

In U.S. Pat. No. 4,610,979 synthetic phospholipid analogs are described for use as pharmaceutically active ingredients for the treatment of asthma. Compositions containing the compounds are administered by enteral, oral, rectal and parenteral routes/though no specific details of any pharmaceutical compositions are given.

In "Platelet Activating Factor—INSERM Symposium No.23" eds Benveniste J and Arnoux B,(1983) pp49–56, Lee et al describe the preparation of an analog of platelet activating factor 1-O-octadecyl-2-deoxy-2-(2'-oxopropyl) rac-glycero-3-phosphorylcholine. An aqueous solution of the analog was administered intravenously to determine the bronchoconstriction properties of the compound.

The present invention relates to materials which comprise a surface having pendant groups of the formula (I)

in which the groups —B— are the same or different, preferably the same, and each is —$CH_2$— or —$C(=O)$—, preferably —$CH_2$—.

$R^1$ is hydrogen alkyl of 1 to 12, preferably 1 to 4 carbon atoms, or a group capable of bonding to, or bonded to, a ligand or $R^1$ is a polymerisable, preferably ethylenically unsaturated, group and Z is a zwitterionic group.

Preferably, in the group of formula (I) $R^1$ is an alkyl group, more preferably methyl.

The present invention also provides use of compounds containing a group of formula (I) in improving the biocompatibility of a surface. It thus relates to a method of improving the biocompatibility of a surface which comprises providing a surface having pendant groups of formula (I).

Groups of formula (I) are not based upon a glycerol-type structure but rather are derivable from a triol having a central, preferably quaternary, carbon atom. Compounds containing such groups possess advantages in that the positions occupied by the groups B on the central carbon atom are equivalent, rendering such compounds easier to prepare and to purify. In particular, where the two group B are attached to oxygen atoms, then these groups are both derived from primary alcohol groups. This makes compounds containing such groups easier to synthesise than compounds derived from a glycerol in which there are primary and secondary hydroxyl groups.

In addition, compounds containing a group of formula (I) in which the two groups attached via B to the central carbon atom are the same are advantageous in that they are achiral and are therefore easier to purify than the corresponding glycerol-based derivatives.

Also, where the group B is ether-linked then compounds containing a group of formula (I) are less subject to hydrolysis than the acyl analogues.

Groups of formula (I) may comprise a conventional phosphoryl choline zwitterionic group or another zwitterionic group which also shows desirable biocompatible properties as is illustrated in the definition of the group Z.

Compounds containing such groups may for instance be analogues of GPC which may be used to coat a surface, polymerisable compounds which are analogues of GPC which may be polymerised or copolymerised to provide a polymer which may be used as a bulk material, or as a surface treatment.

The present invention therefore further provides polymers obtainable by the polymerisation or copolymerisation of compounds containing the group of formula (I). Such polymers, may in particular be polyesters or polyurethanes which contain residues of compounds containing a group of formula (I) in which the groups B are bonded to hydroxyl groups or to hydroxyalkyl groups preferably of 1 to 6 carbon atoms. Other types of polymers which contain residues of compounds containing a group of formula (I) may be prepared and used as bulk materials.

Further such polymers may comprise residues of a compound containing a group of formula (I) which contains an ethylenically unsaturated polymerisable group such as an acrylate, acrylamide, alkacrylate for example methacrylate, alkacrylamide for example methacrylamide, styrene or vinyl group attached to at least one of the groups B. Such polymers are particularly suitable for use as surface treatments.

Such polymers may alternatively comprise the residues of compounds containing a group of formula (I) in which $R^1$ is a polymerisable group. In such a case, $R^1$ may comprise a spacer group, such as alkylene of 1 to 12, preferably 2 to 4 carbon atoms linked to the polymerisable group. Suitable polymerisable groups include vinyl, styrene, acrylate, alkacrylate, acrylamide and alkacrylamide groups. Of these, preferred groups include styrene, acrylate, alkacrylate of 1 to 4 carbon atoms in the alkyl group preferably methacrylate, acrylamide and alkacrylamide of 1 to 4 carbon atoms in the alkyl group.

Alternatively, compounds containing a group of formula (I) may be activated derivatives of GPC analogues which may bind covalently to a surface to improve biocompatibility and compounds comprising a group of formula (I) may be used as additives for polymers to improve the biocompatibility of the polymer. GPC analogues containing groups of formula (I) may also be used to form ordered arrays such as liposomes or monolayers.

Compounds containing a group of formula (I) may be used to improve the biocompatibility of a surface. They may be used to improve haemocompatibility or to reduce the tendency of protein to be absorbed at a surface. In addition, they may be used to reduce the tendency of microorganisms, such as bacteria, yeast, algae or fungi and in particular bacteria, to adhere to the surface. They may also be used more generally to reduce cellular adhesion at a surface. Surfaces treated with such compounds therefore have a wide variety of applications in the medical field such as in blood-contacting devices, in the treatment of contact lenses and also in domestic or industrial fields wherever it is desired to reduce the adhesion of protein or microorganisms at a surface.

In addition groups of formula (I) may be used for the attachment of a ligand to a surface having such pendant groups. The term ligand includes, but is not limited to, specific binding agents such as immunoglobulins and associated fragments thereof such as those useful for affinity separation and diagnostic applications, photosensitive and chemosensitive moieties such as those useful for detector and sensor applications and therapeutic agents, such as peptide fragments, useful for clinical applications. Other ligands include peptide fragments which may be chemically linked to a group of formula (I) such as fragments which induce cell attachment and may therefore be used to provide cell seeding.

Where it is desired to attach a ligand to a group of formula (I) then preferably in the group of formula (I) $R^1$ is amine, hydroxyl or carboxylic acid (or activated derivative thereof), or $R^1$ contains such an amine, hydroxyl or carboxylic acid (or activated derivative thereof) group separated from the central carbon atom by a spacer group. Where such a spacer group is used then it will be of sufficient length to allow the functional group in $R^1$ to interact with ligand. Examples of suitable spacer groups include alkylene, preferably of 1 to 12, more preferably 2 to 4, carbon atoms. It will be appreciated that where $R^1$ comprises amine or carboxylic acid then this may be in the form of a salt.

It will be appreciated that where it is desired to control the number of sites of attachment of such a ligand to a surface then a mixture of compounds containing a group of formula (I) may be used containing a proportion of a compound in which $R^1$ is a group able to bind a ligand moiety and a compound containing a group of formula (I) where $R^1$ is hydrogen or alkyl. Ligands may also be attached to other moieties of the compounds containing a group of formula (I) which are suitable for such attachment. Alternatively, compounds containing a group of formula (I) may be used together with other compounds able to provide a suitable site of attachment for a ligand to provide a biocompatible surface to which ligands may be attached.

As a further feature the present invention provides compounds containing a group of formula (I) which are achiral. In such compounds, the groups B are the same and are attached to identical groups or alternatively to a single group which forms an achiral cyclic structure with the groups B and the central carbon atom.

Preferred compounds of the present invention are of the formula (IA)

in which $R^1$, B and Z are as hereinbefore defined, the groups $R^2$ are the same and each is hydrogen, alkyl, alkenyl or alkynyl of up to 25 carbon atoms, optionally containing one or more etheric oxygen atoms and unsubstituted or substituted by one or more fluorine atoms and/or functional groups capable of reacting to provide covalent attachment to a surface and/or polymerisable groups or the groups $R^2$ are silicon-oxygen-containing chains, such as siloxane groups, and the groups Y are the same and each is a valence bond or a linking group selected from —I—, —S—, —NH—, —OC(O)—, —C(O)—O—, —SC(O)—, —C(O)—S—, —NHC(O)—, —C(O)—NH—, —OC(O)O—, —SC(O) O—, —NHC(O)—, —OC(O)S—, —SC(O)S—, —NHC(O)S—, —OC(O)NH—, —SC(O)NH— and —NHC(O) NH—.

Preferably Y is other than a valence bond, more preferably —O—, —S— or —NH—. Most preferably Y is —O—. Such compounds, and in particular those in which Y is —O— are particularly preferred since they are not susceptible to hydrolysis at an ester or amide linkage as may occur in the glycerol-based derivatives of the prior art referred to above. In one embodiment, $R^2$ is hydrogen. Such compounds of formula (IA) are particularly useful as intermediates in the preparation of other compounds containing a group of formula (I), such as compounds of formula (IA) in which $R^2$ is alkyl, alkenyl or alkynyl. Preferably, when $R^2$ is hydrogen Y is —O— or —NH— and more preferably B is —CH$_2$— so that the compound of formula (IA) is a diol or diamine. Such compounds are particularly useful as monomers which may be used to form polymers such as polyesters, polyurethanes and polyamides containing pendant groups of formula (I).

In a second embodiment $R^2$ is alkyl, alkyenyl or alkynyl containing from 8 to 20, more preferably 12 to 18 and most preferably 16 carbon atoms each. Where a group $R^2$ contains ethylenic unsaturation then it may contain one or more carbon-carbon double or triple bonds which are either conjugated or unconjugated.

In one particular embodiment a group $R^2$ contains two or more conjugated triple bonds which, upon irradiation may be used to provide cross-linking intra- or inter-molecularly within the coating in the manner described in EP-A-32622. Such compounds are also particularly suitable for forming liposomes in the manner described in EP-A-32622 and EP-A-161759.

In another particular embodiment $R^2$ is a saturated straight-chain alkyl group.

Alternatively, $R^2$ may be substituted by a functional group such as amino, carboxylate, isocyanate, thiol, or hydroxy group or an activated derivative thereof capable of providing covalent attachment of the compound of formula (IA) to a surface. Such a group may for example be an amino or carboxylate group. Preferably, the group $R^2$ provides a spacer group, which is an alkylene, alkenylene, or alkynylene group between the residue of formula (I) and the functional group. Such a spacer preferably contains from 1 to 12, more preferably 2 to 4, carbon atoms and is preferably an alkylene group.

In a further alternative, $R^2$ is substituted by a polymerisable group. Such a polymerisable group may for a vinyl, styrene, acrylate, alkacrylate, acrylamide and alkacrylamide groups. Of these, preferred groups include styrene, acrylate, alkacrylate of 1 to 4 carbon atoms in the alkyl group, preferably methacrylate, acrylamide and alkacrylamide of 1 to 4 carbon atoms in the alkyl group. Preferably, the group $R^2$ provides a spacer group, which is an alkylene, alkenylene, or alkynylene group between the residue of formula (I) and the polymerisable group. Such a spacer preferably contains from 1 to 12, more preferably 2 to 4, carbon atoms and is preferably an alkylene group.

In a further aspect the present invention relates to polymers and copolymers obtainable by polymerisation or copolymerisation of a compound of formula (IA) in which either $R^1$ or $R^2$ is a polymerisable group.

Zwitterionic Groups

As examples of zwitterionic groups Z which may be present in the compounds of formula (I) mention is made of groups which contain, as anion, a phosphate, sulphonate, carboxylate or phosphate-ester group (or groups in which one or more of the ester oxygen atoms of a phosphate ester are replaced by —S—, —NH— or by a valence bond) and which contain, as cation, ammonium, phosphonium or sulphonium.

Type A

In one specific embodiment, the zwitterionic group Z comprises as anion a phosphate ester, or derivative thereof in which one or more of the ester oxygen atoms is replaced, and as cation an ammonium, phosphonium or sulphonium, preferably ammonium, moiety. Such groups are preferably of the formula (II)

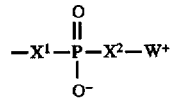
(II)

in which the moieties $X^1$ and $X^2$, which are the same or different, are —O—, —S—, —NH— or a valence bond, preferably —O—, and W is a group containing an ammonium, phosphonium or sulphonium, preferably an ammonium, more preferably a quaternary ammonium, cation.

The group $W^+$ may for example be a group of formula —$W^1$—$N^+R^3{}_3$, —$W_1$—$P^+R^{3a}{}_3$ or —$W^1$—$S^+R^3{}_2$ or —$W^1$—Het in which:

$W^1$ is alkylene optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and the groups $R^3$ are the same or different and each is hydrogen or alkyl of 1 to 4 carbon atoms, preferably methyl, or aryl, such as phenyl, or two of the groups $R^3$ together with the nitrogen atom to which they are attached form a heterocyclic ring containing from 5 to 7 atoms or the three groups $R^3$ together with the nitrogen atom to which they are attached form a fused ring structure containing from 5 to 7 atoms in each ring, and optionally one or more of the groups $R^3$ is substituted by a hydrophilic functional group; and the groups $R^{3a}$ are the same or different and each is as defined for $R^3$ or is a group $OR^3$ where $R^3$ is as defined above; or Het is an aromatic nitrogen-, phosphorus- or sulphur-, preferably nitrogen-, containing ring, for example pyridine.

Compounds in which one or more of the groups $R^3$ are substituted by a hydrophilic group are particularly suitable for providing a surface with an increased water content. Suitable functional groups include hydroxy, amine and carboxyl groups. Preferably however $R^3$ is not substituted by such groups.

Alternatively, $W^+$ may itself be a heterocyclic group containing a nitrogen, phosphorus or sulphur atom, for example a heterocycle containing from 5 to 7 atoms preferably including a quaternised nitrogen atom.

Where W is a group —$W^1N^+R^3{}_3$, —$W^1$—$P^+R^{3a}{}_3$, —$W^1$—$S^+R^3{}_2$ or —$W^1Het^+$ preferably the group $W^1$ contains up to 20 carbon atoms, more preferably up to 12 carbon atoms. In one embodiment $W^1$ contains 6 or more carbon atoms.

Preferably $W^1$ is a straight-chain alkylene group. In one specific embodiment $W^1$ is a group —$CH_2CH_2$—.

Where $W^1$ contains a cycloalkyl group, preferably the cycloalkyl group contains from 5 to 7, more preferably 6, carbon atoms in the ring. Where $W^1$ contains an aryl group this may for example be phenyl unsubstituted or substituted by for example one or more alkyl groups of 1 to 4 carbon atoms.

Compounds containing a group of formula (II) may be obtained by the reaction of an analogous compound containing a group of formula (IIA)

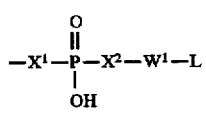
(IIA)

in which $W^1$, $X^1$ and $X^2$ are as hereinbefore defined, L is a displaceable leaving group such as halogen, alkylsulphonyloxy or arylsulphonyloxy, with a compound of formula $NR^3{}_3$ $PR^{3a}{}_3$, $SR^3{}_2$ or Het as defined above. The reaction is generally performed in an organic solvent, such as chloroform or acetonitrile and at a temperature from room temperature to 120° C., for example in a sealed vessel.

Compounds containing a group of formula (IIA) may be obtained by the reaction of a compound of formula (III)

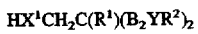
(III)

in which $R^1$, $R^2$, B, $X^1$ and Y are as hereinbefore defined, or where $X^1$ is a valence bond, an analogue of a compound of formula (III) with an organometallic group in place of HX¹—, with a compound of formula (IV)

$$Cl_2P(O)X^2{-}W^1{-}L \qquad (IV)$$

in which $W^1$, $X^2$ and L are as hereinbefore defined.

The reaction is generally performed in anhydrous conditions in the presence of an organic solvent, such as ether, and in the presence of a base such as triethylamine. The reaction is typically performed at a temperature from room temperature to 80° C. In the case where $X^1$ is a valence bond compounds of formula (IIA) may be obtained by reaction of the organometallic derivative with a compound of formula (IV), by known methodology.

Compounds of formula (III) and organometallic analogues thereof may be obtained by derivatisation of a compound of formula (V)

$$HX^1CH_2C(R^1)(B_2YH)_2 \qquad (V)$$

in which $R^1$, B, $X^1$ and Y are as hereinbefore defined and are preferably the same. Compounds of formula (V) are for example triols, trithiols or triamines which are commercially available or may be obtained using standard methods.

Compounds of formula (IV) may also be obtained according to standard methods and in particular by methods described in the Examples which follow or by analogous methods.

Alternatively, compounds containing a group of formula (II) in which W is $-W^1-N^+R^3_3$, may be obtained by derivatisation, for example by reaction with an alkyl halide, of a corresponding compound bearing a group $-W^1-NR^3_2$ in place of the group W. The reaction may for example be carried out in the presence of a base, such as potassium carbonate, in an organic solvent such as dichloromethane at a temperature from 0° to 50° C.

Compounds bearing a group $W^1-NR^3_2$ may be obtained by methods analogous to those used to obtain compounds containing a group of formula (IIA) described above. This methodology is illustrated in Example 3 which follows.

Compounds containing a group of formula (II) in which W is $-W^1-P^+R^{3a}_3$ or $-W^1-S^+R^3_2$ may be prepared in analogous manner from compounds bearing a group $-W^1-PR^{3a}$ or $-W^1-SR^3_2$ respectively.

Compounds containing a group of formula (II) may alternatively be prepared by analogy with the route described in Example 9 which follows.

Type B

Further Examples of the zwitterionic groups Z which may be present in the compounds of formula (I) are groups of formula (VI)

$$-X^3-R^4-N^+(R^5)_2-R^6-V \qquad (VI)$$

in which $X^3$ is a valence bond, —O—, —S— or —NH—, preferably —O—;

V is a carboxylate, sulphonate or phosphate anion;

$R^4$ is a valence bond (together with $X^3$) or alkylene, —C(O)alkylene- or —C(O)NHalkylene, preferably alkylene and preferably containing from 1 to 6 carbon atoms in the alkylene chain;

the groups $R^5$ are the same or different and each is hydrogen or alkyl of 1 to 4 carbon atoms or the groups $R^5$ together with the nitrogen to which they are attached form a heterocyclic ring of 5 to 7 atoms; and $R^6$ is alkylene of 1 to 20, preferably 1 to 10, more preferably 1 to 6 carbon atoms.

Compounds containing a group of formula (VI) in which $R^4$ and $X^3$ are together a valence bond, may be obtained by reaction of a compound of formula $R^5_2NR^6V$ with a compound of formula (III) or a derivative thereof bearing a leaving group in place of the group $HX^1$. Compounds containing a group of formula (VI) in which $R^4$ is other than a valence bond may be obtained using spacer chemistry according to standard methods, using an ether (or sulphide or secondary amine), ester (thioester or amide) or carbonate (thiocarbonate or urea derivative). This may include the use of a Michael acceptor (for example an acrylate) which undergoes reaction with secondary amines (for example N-methyl glycine) to give a tertiary amine and is then alkylated to give the final product.

Type C

Further examples of zwitterionic groups which may be present in the compounds of formula (I) are the groups of formula (VII)

$$-X^4-R^7-CHCO_2^- \atop {\ \ |\ \ \atop ^+NR^8_3} \qquad (VII)$$

in which $X^4$ is a valence bond, —O—, —S— or —NH—, preferably —O—, $R^7$ is a valence bond (optionally together with $X^4$) or alkylene, —C(O) alkylene- or —C(O)NHalkylene, preferably alkylene and preferably containing from 1 to 6 carbon atoms; and the groups $R^8$ are the same or different and each is hydrogen or alkyl of 1 to 4 carbon atoms, preferably methyl, or two of the groups $R^8$, together with the nitrogen to which they are attached, form a heterocyclic ring of from 5 to 7 atoms, or all three groups $R^8$ together with the nitrogen atom to which they are attached form a fused ring structure containing from 5 to 7 atoms in each ring.

Compounds containing a group of formula (VII) may be obtained by reacting a compound of formula (III) with a compound of formula (VIIA)

$$L^1-X^4-R^7-CH(N^+R^8_3)CO_2^- \qquad (VIIA)$$

wherein $X^4$, $R^7$ and $R^8$ are defined in relation to formula (VII) and $L^1$ is a carboxylic acid group or activated derivative thereof.

Type D

Further examples of the zwitterionic group Z which may be present in the compound of formula (I) are the groups of formula (VIII)

$$-X^5-R^9-C(U^-)-R^{10}-W^{2+} \qquad (VIII)$$

in which $X^5$ is —O—, —S—, NH—, —OC(O)—, —NHC(O)—, or —SC(O)—, $R^9$ and $R^{10}$ are the same or different and each is alkylene of 1 to 20, preferably 1 to 10 carbon atoms, U is carboxylate, phosphate, sulphonate or oxime and $W^2$ is an ammonium, phosphonium or sulphonium, preferably an ammonium, group.

Preferably $X^5$ is —OC(O), —NHYC(O) or —SC(O), more preferably —OC(O)—.

Compounds containing a group of formula (VIII) may be obtained by the reaction of an amine, phosphine or sulphide with a corresponding compound containing a group of formula (VIIIA)

$$-X^5-R^9-C(U^-)-R^{10}-Hal \qquad (VIIIA)$$

in which $X^5$, U, $R^9$ and $R^{10}$ are as hereinbefore defined and Hal is halogen.

Compounds containing a group of formula (VIIIA) in which U is oxime may be obtained from the corresponding compound bearing a carbonyl group in place of the group U and compounds in which U is phosphate or sulphonate may be obtained by reaction of a corresponding compound bearing a hydroxyl group in place of the group U with a phosphorous oxychloride or sulphonylchloride followed by hydrolysis. The compounds bearing hydroxyl or carbonyl in place of the group U may be obtained by reaction from a compound of formula (III).

Materials comprising a surface having pendant groups of formula (I) may be used to provide a surface having improved biocompatibility, haemocompatibility and/or ocular compatibility. In particular such materials may show minimal interaction with biological systems such as blood, urine, tear films or tissue fluid. Such surfaces exhibit a reduced tendency for example to protein adhesion or interaction with blood cells such as platelets, at the surface or reduced tendency to adhesion by microorganisms, such as bacteria. Such a surface may be provided by treating, for example coating, a surface with a compound containing a group of formula (I) or by providing a bulk material which comprises groups of formula (I).

In one aspect, the present invention provides a process for producing a material of the present invention which comprises (a) treating a surface of a substrate with a compound containing a group of formula (I) or (b) using a compound containing a group of formula (I) to produce a material comprising pendant groups of formula (I) at the surface and in the bulk of the material.

Such a surface treatment process may be performed using solution or dispersion of the compound. Preferred solvents which may be used include lower alkanols such as methanol, ethanol and iso- or n-propanol, halogenated alkanes such as chloroform and mixtures thereof. After coating, the solvent may be removed by conventional techniques, for example by evaporation or under reduced or ambient pressure in a gas stream and/or at elevated temperature. By careful selection of the solvent, the concentration of the compound and thickness of the coating may be controlled.

The surface of the substrate may, if desired, be pre-washed using a suitable solvent which may be the same or different to the solvent used in coating. Pre-treatment of the surface by silylation or other means may be used.

Where necessary the surface of the substrate may be functionalised prior to treatment. This can be effected by known etching or derivatising techniques, such as plasma discharge, which introduce the appropriate surface functionality (see for example "Chemical Reactions of Polymers" Ed. E. M. Fettes, 1964, Interscience, London)

Materials may be coated by known techniques, such as dip-coating, spray-coating, web-coating or spin coating.

Where a material comprising groups of formula (I) in both the surface and bulk of the material is to be fabricated, then this may be performed using known conventional methodology for the fabrication of such materials, for example by the polymerisation, or copolymerisation fo a polymerisable compound containing a group of formula (I) and optionally using known moulding or shaping techniques.

Materials having surfaces which comprise groups of formula (I), may in particular be obtained by analogy with the use of GPC derivatives as described in patent applications WO-A-02933, WO-A-87/0284, WO-A-88/00956, WO-A-91/13639, WO-A-92/07885, WO-A-93/01221, or PCT/GB92/01580, the contents of which are incorporated herein by reference. By proceeding in a manner analogous to that described in any of those applications, a material may be obtained comprising a surface treated with a polymeric or non-polymeric compound comprising a group of formula (I) or else a bulk material comprising groups of formula (I).

Materials having surfaces comprising groups of formula (I) can be used as a construction material for implants or prostheses for the human or animal body, particularly where these implants or prostheses are to come into direct physical contact with blood and where biocompatibility and particularly haemocompatibility are required e.g. in heart valves. They can also be used in the construction of membranes and other devices that are to be brought into contact with blood or other body fluids on an extra-corporeal basis, for example in heart-lung machines or artificial kidneys.

Additionally materials of the invention may be employed in processing applications e.g. separation membranes and process equipment and tubing. In particular they can be used to modify the surface properties of biofiltration membranes in bioreactors and fermentation systems, where the membranes come into direct contact with complex biological solutions containing e.g. proteins, polysaccharides, fats and even whole cells.

The present invention also relates to a process for producing a shaped article which comprises shaping an article from material comprising a surface having pendant groups of formula (I). It further relates to a shaped article comprising a material having a surface comprising pendant groups of formula (I).

In addition, the present invention can be used to provide finished implants, prostheses, membranes, catheters, contact lenses, intraocular lenses, and other devices which comprise a surface having pendant groups of formula (I) and thus to impart biocompatibility to the article.

The invention thus also provides a finished device comprising a surface comprising groups of formula (I). When materials of the invention are used in the construction of finished devices, it may be necessary to take precautionary steps to ensure that the surface is not damaged and the effectiveness of the treatment reduced before the finished device is produced. Such a device may be fabricated using known conventional methodology.

The present invention will now be illustrated by the following Examples.

EXAMPLES

The following assays have been used to evaluate coatings of compounds according to the present invention.

Protein adsorption using an enzyme immunoassay

The assay determines absorption of human fibrinogen at a surface. This protein is representative of protein which is typically adsorbed at a surface. The assay can be readily modified to determine the absorption of other proteins.

Polyethylene tubing was coated with a sample and human plasma (5 ml) was pumped through the tubing using a Watson-Marlow multi-head peristaltic pump (lowest setting). The tubing was then washed by pumping through phosphate buffered saline (PBS) (×2). A solution containing antibodies specific to human fibrinogen (5 ml) was then pumped through followed by a further wash of PBS (×2). A conjugate of horseradish peroxidase and a second antibody specific to the first fibrinogen-specific antibody (5 ml) was passed through followed by a further wash of PBS (×2). O-Phenylene diamine in phosphate-citrate buffer (5 ml), (0.8 mg/ml) was passed through and the adsorption at 450 nm was read using a microplate reader.

Results are calculated as the percentage reduction in adsorption at 450 nm compared to an untreated sample of polyethylene tubing. As a control for non-specific binding of antibody to the samples each sample was also incubated with non-specific antibody.

Activated Platelet Study

Blood was collected from a healthy adult volunteer using the double syringe method where the first 5ml of blood is discarded. The blood was collected into tri-sodium citrate (32 g/l) in the proportion of 9 volumes to 1 volume citrate in plastic tubes. The samples were kept at room temperature on a spiral mixer until used.

Samples of polyethylene ribbon were treated with sample compound as described below and untreated polyethylene ribbon were used as controls.

Half of the test samples were incubated with citrated blood (200 µl) and the remainder were incubated with EDTA-treated blood on a phase shaker for 30 minutes before washing in PBS four times. Platelet activation was measured in a manner similar to that described above for detection of proteins by enzyme immunoassay using antibodies against GMP140 to detect the presence of this platelet activation marker on the surface of biomaterials. In the presence of EDTA, which extracts calcium from inside platelets, activation is inhibited, so that incubation with EDTA-treated blood acts as a non-specific control for activation, obviating the need for incubation in non-specific antibody.

C-Reactive protein (CRP) binding assay

C-reactive protein is a protein which binds specifically to isolated ammonium phosphate ester groups e.g. phosphoryl choline groups which are attached to a surface.

Samples of polyethylene ribbon treated with a sample compound and untreated ribbon (as control) were incubated for 10 minutes at ambient temperature in a protein solution consisting of bovine serum albumin (BSA) (40 mg/ml) and CRP (0.012 mg/ml) in HEPES-buffered saline and containing calcium chloride (1 mM).

After incubation, the samples were washed in phosphate buffered saline (PBS) and then incubated for 30 minutes in a solution containing anti-CRP human antibody. After washing with PBS, the samples were incubated with anti-IgG antibody conjugated with horseradish peroxidase in PBS. The samples were washed three times in PBS as before and transferred to new microplates. A solution of O-phenylene diamine (OPD, 0.4 mg/ml) in phosphate-citrate buffer was added and the reaction allowed to proceed for ten minutes. At this time an aliquot of the mixture in each of the wells was transferred to a new well, and the optical density of the solutions measured using an automated plate reader at 450 nm using the OPD solution as a blank.

Percentage reduction in Phospholipase C

The compound under study (0.001 mmole), in a glass vial, was dissolved in ether (2 ml) and tris acetate buffer (0.1M, pH 7.4, 1 ml) containing calcium chloride (10 mM) was added. Phospholipase C (Type XIV, from *C. Perfringens*, 2 units) as a solution in the acetate/calcium chloride buffer (0.114 ml) was added, the reaction vessel was sealed and vigourously shaken at 37+ C. for 16 hours. The layers were allowed to settle and the organic extract was assayed by thin layer chromatography, eluting with chloroform:methanol; aqueous ammonia (25%), (690:270:64). The spots were developed using phosphomolybdic acid spray and a semi quantitative value on the extent of hydrolysis was made by comparison with dipalmitoyl phosphatidyl choline which had been subject to the same procedure.

Percentage reduction in Phospholipase D

To the compound under study (0.001 mmole), in a glass vial, was added sodium acetate buffer (0.4M, pH 8.0, 0.2 ml), aqueous calcium chloride (0.2M, 0.2 ml) and phospholipase D (Type VI, from Streptomyces Chromromofuscus, 31 units) as a solution in acetate buffer (0.02 ml). Ether (0.5 ml) was added and the mixture was incubated at 30° C. for sixteen hours. Hydrochloric acid (1M, 0.1 ml) was added to quench the reaction, followed by a mixture of ether:ethanol (4:1) (2 ml). The organic layer was assayed by thin layer chromatography, eluting with chloroform:methanol; aqueous ammonia (25%), (690:270:64). The spots were developed using phosphomolybdic acid spray and a semi-quantitative value on the extent of hydrolysis was made by comparison with dipalmitoyl phosphatidyl choline which had been subject to the same procedure.

Example 1

1,3-dihexadecyloxy-2-(hydroxymethyl)-2-methyl propane

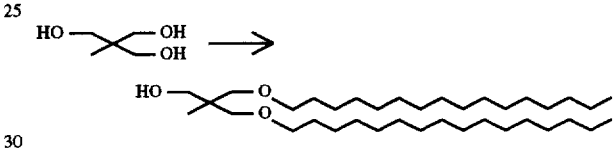

Sodium hydride (washed with petroleum ether, 60% dispersion, 20 g, 0.5 mole) was dissolved in dry dimethyl formamide (200 ml). Tris(hydroxymethyl)ethane (30 g, 0.25 moles) was added and the mixture stirred for one hour before 1-bromohexadecane (168 g, 0.55 mole) was added and after warming to 50° C. was stirred for 44 hours. After cooling to room temperature the mixture was partitioned between dichloromethane and water. The organic layer was washed successively with water, hydrochloric acid (0.1M) and brine before drying over sodium sulphate and evaporating to a crude waxy solid, 150g.

This material was purified, when required, in 20 g batches eluting with petroleum ether (40–60): ethyl acetate (9:1). Fractions containing the desired compound were combined and evaporated to give pure 1,3-dihexadecyloxy-2-(hydroxymethyl)-2-methyl propane (hereinafter referred to in the Examples as Compound A).

$^1$H-nmr (200 MHz, CDCl$_3$), 0.88 (9H, m), 1.30 (52H, m), 1.55 (4H, m), 3.2 (1H, t), 3.5 (8H, m), 3.55 (2H, d).

Example 2

1,3-dihexadecyloxy-2-(hydroxymethyl {[hydroxyphosphinyl)oxy]-N,N,N-trimethylethaminium hydroxide, inner salt}) 2-methyl propane.

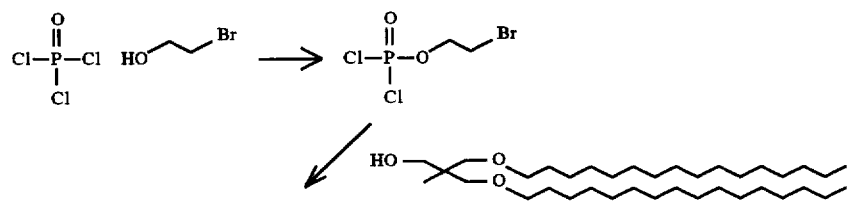

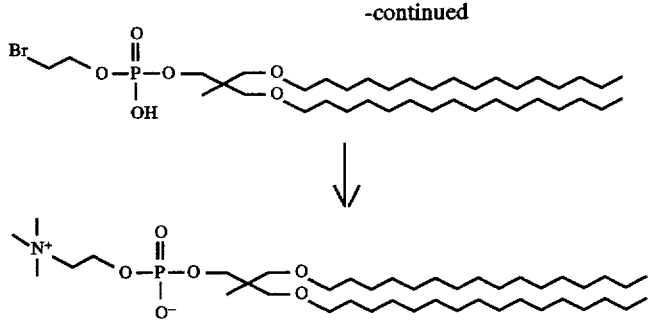

Bromoethanol (distilled, 9.59, 76 mmole) was added dropwise to phosphorus oxychloride (11.19, 76 mmole), dropwise in dichloromethane (30 ml) over 30 minutes under nitrogen. The mixture was stirred at room temperature under nitrogen for 16 hours. The mixture was evaporated down and dried under vacuum to yield crude [2-bromoethyl] dichlorophosphate which was distilled under vacuum to give pure compound, 4.4 g, 21 mmole, 28% yield.

$^1$H-nmr (200 MHz, CDCl$_3$), 3.65 (2H, t), 4.60 (2H, m).

Compound A (0.5 g, 0.88 mmole) was dissolved in anhydrous ether (10 ml) and triethylamine (152 mg, 1.5 mmole) was added. Over a minute [2-bromoethyl] dichlorophosphate (338 mg, 1.5 mmole) was added and refluxed for 16 hours. Triethylamine (304 mg, 3 mmole) was added together with water (2 g, 111 mmole) and the mixture heated at 50° C. for two hours.

After cooling, the solvent was removed under reduced pressure and the residue azeotroped with benzene. The residue was dissolved in ether and the mixture filtered to remove solid residues. The ethereal solution was evaporated to dryness, the residue dissolved in chloroform (5 ml) and added to a solution of trimethylamine (1.5 g, 25 mmole) in acetonitrile (15 ml) which was heated at 60° C. for 16 hours. After cooling, the mixture was left at −20° C. for 30 minutes, when a white solid was filtered off, which contained crude product by tlc (CHCl$_3$:MeOH:25% NH$_3$, 690:270:64). The product was chromatographed on silica gel (30g) eluting with solvent ranging from chloroform to chloroform:methanol:25% ammonia, 690:270:64. Fractions containing product were combined, and evaporated to white solid which was azeotroped with benzene and dried under reduced pressure over phosphorus pentoxide to give 1,3-dihexadecyloxy-2-(hydroxymethyl{[(hydroxyphosphinyl)oxy]N,N,N-trimethylethaminium hydroxide, inner salt}) 2-methyl propane, 240 mg, 0.3 mmole, 38% yield.

$^1$H-nmr (300 MHz, CDCl$_3$), 0.88 (6H, t), 0.93 (3H, s), 1.26 (52H, m), 1.50 (4H, m), 3.26 (4H, s), 3.34 (4H, t), 3.42 (9H, s), 3.68 (2H, m) 3.84 (2H, m), 4.29 (2H, m).

Mass Spectrum: (FAB +ve ion m-nitrobenzylalcohol matrix) M+=734.

The compound, when coated on polyethylene tubing, in accordance with the method described in Example 7, showed a 94% reduction in fibrinogen adsorption and when coated on polyethylene ribbon in accordance with Example 8 showed a 100% reduction in activation of blood platelet and no interaction with C-reactive protein.

By proceeding in an analogous manner using dimethylamine in place of trimethylamine, an analogous compound was prepared in which the group Me$_3$N$^+$-group was replaced by Me$_2$HN$^+$—. This compound, when coated onto polyethylene tubing showed a reduction in fibrinogen adsorption of 88%.

Example 3

1,3-dihexadecyloxy-2-(hydroxymethyl {[1-hydroxyphosphoryl)oxy]3[N, N, N trimethylaminium] phenyl hydroxide, inner salt}) 2-methylpropane

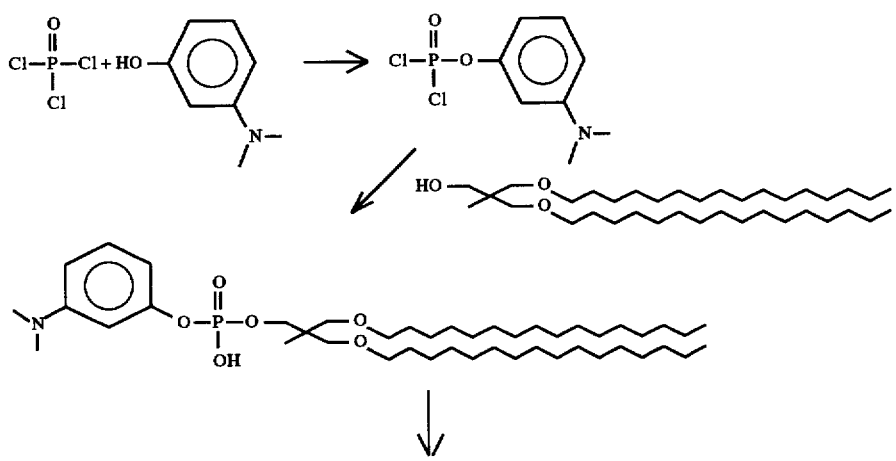

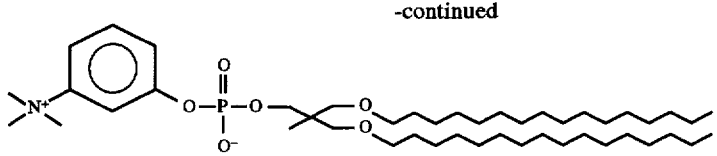

3-Dimethylaminophenol (2 g, 14.6 mmole) in dichloromethane was added over thirty minutes to phosphorus oxychloride (2.24 g, 14.6 mole) in dichloromethane. The mixture was stirred under nitrogen for 16 hours when further phosphorus oxychloride (2.24 g, 14.6 mmole) was added. After two hours, the reaction mixture was evaporated to dryness and azeotroped with benzene (×1) before drying under high vacuum, to give the crude dichlorophosphate.

Triethylamine (0.36 g, 3.5 mmole) and dichlorophosphate (1.89 g, 7.4 mmole) were added to Compound A (1 g, 1.75 mmole) in chloroform (ethanol free). The mixture was stirred at 50° C. for 16 hours. Water (1.89 g, 105 mmole) and triethylamine (0.36 g, 3.5 mmole) were added and the mixture refluxed for two hours. After cooling, the aqueous layer was removed and the organic layer evaporated to dryness, azeotroped with benzene and dried under reduced pressure. The crude material was partially purified by column chromatography, eluting with chloroform:methanol (5:1, containing a trace of acetic acid) to give the intermediate tertiary amine shown above (0.18 g).

Potassium carbonate (45 mg, 0.3 mmole) and 18-Crown-6 (85 mg, 0.3 mmole) were stirred in dichloromethane (4 ml) for 20 minutes. To this was added the tertiary amine produced above (0.18 g) in dichloromethane followed by iodomethane (0.18 g, 1.2 mmole) which was sealed under nitrogen and stirred at ambient temperature overnight.

The mixture was poured into water and extracted into chloroform (×3). After drying (sodium sulphate) the mixture was filtered and evaporated to a crude residue which was chromatographed on silica gel, eluting with solvent ranging from chloroform to chloroform:methanol (1:1) to give 1,3-dihexadecyloxy-2-(hydroxymethyl {[1-hydroxyphosphoryl)oxy]3[N, N, N trimethylaminium]phenyl hydroxide, inner salt}) 2-methylpropane, 50 mg, 0.064 mmole, 4% yield.

$^1$H-nmr (200 MHz, CDCl$_3$), 0.90 (9H, m), 1.26 (52H, m), 1.50 (4H, m), 3.26 (4H, s), 3.35 (4H, t), 3.70 (9H, s), 3.9 (2H, d), 7.2–7.4 (3H, m), 3.85 (1H, s).

$^{13}$C-nmr (50 MHz): 14.1, 17.1, 22.7, 26.2, 26.4, 29.3, 29.5, 29.7, 29.9, 30.3, 31.9, 40.7, 40.8, 57.2, 69.01, 69.1, 72.9, 73.1, 112.4, 122.6, 130.6, 147.3, 155.4, 155.5.

Mass Spectrum: (FAB +ve ion m-nitrobenzyl alcohol matrix) M+1=782.

This compound when coated on polyethylene tubing in accordance with Example 7 showed a reduction in fibrinogen adsorption of 89%.

When incubated with phospholipase D this compound showed a similar propensity to hydrolysis as conventional phospholipids.

Example 4

1,3-dihexadecyloxy-2-(hydroxymethyl {[(hydroxyphosphinyl)oxy]N-pyridinium-2-ethyl hydroxide, inner salt}) 2-methyl propane

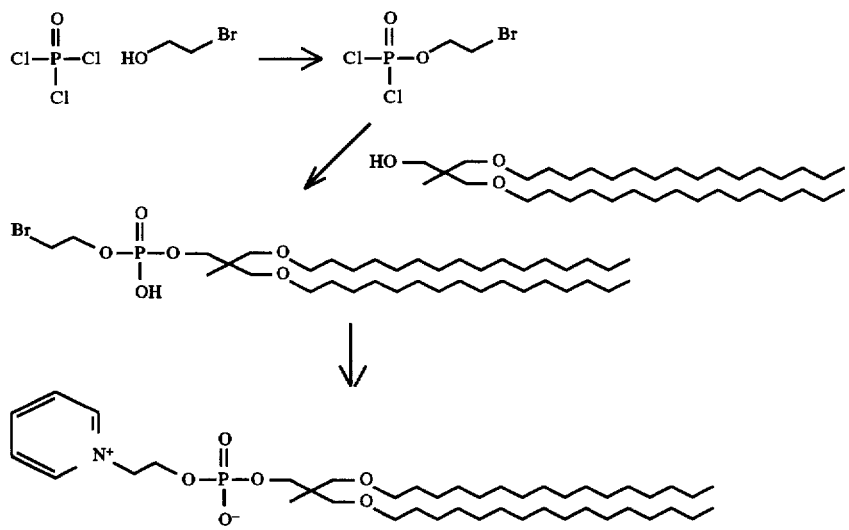

Triethylamine (1.44 g, 14.2 mmole) and [bromoethyl] dichlorophosphate (3 g, 14.2 mmole) (which may be prepared as described in Example 2) were added dropwise over two minutes under nitrogen to Compound A (2.38 g, 4.2 mmole) in dry ether (40 ml). The mixture was heated at 60° C. under nitrogen for 16 hours before triethylamine (1.4 g, 14.2 mmole) and water (9.8 ml) were added and heating maintained for a further two hours. After cooling, the aqueous layer was removed and the residue evaporated to dryness and azeotroped with benzene (×3). The residue was dissolved in ether, filtered and evaporated to give a crude product, 3.5 g. The mixture was chromatographed on silica gel eluting with chloroform:methanol:25% ammonia (690:270:64). Fractions containing partially purified material were combined and evaporated to give the intermediate bromo-compound shown in the scheme above, 2.2 g, 2.9 mmole, 69% yield. Pyridine (6.3 g, 79 mmole) was added to the intermediate thus prepared (2 g, 2.6 mmole) in dry chloroform (15 ml). The mixture was heated at 60° C. for 16 hours before it was cooled and the solvents evaporated under reduced pressure. The residue was chromatographed on silica gel eluting with chloroform:methanol (3:1) to chloroform:methanol:water (65:25:4). Fractions containing the desired compound were combined and evaporated under reduced pressure to give 1,3-dihexadecyloxy-2-(hydroxymethyl{[(hydroxyphosphinyl)oxy]N-pyridinium-2-ethyl hydroxide, inner salt}) 2-methyl propane, 140 mg, 0.19 mmole, 7% yield.

$^1$H-nmr (200 MHz, CDCl$_3$), 0.90 (9H, m), 1.1–1.7, (56H, m), 3.25 (4H, 5), 3.35 (4H, t), 3.65 (2H, d), 4.25 (2H, m), 4.80 (2H, m), 8.05 (2H, t), 8.45 (1H, t), 8.95 (2H, d).

$^{13}$C-nmr CDCl$_3$/CD$_3$OD) 14.0, 16.9, 22.6, 26.1, 28.7, 29.7, 31.9, 40.5, 40.7, 48.7, 49.2, 49.6, 62.2, 63.3, 68.5, 68.6, 71.6, 72.8, 76.4, 77.0, 77.7, 128.1, 145.2, 145.5.

Mass Spectrum: (FAB +ve ion m-nitrobenzylalcohol) M+1=754.

The product thus obtained, when coated on polyethylene tubing in the manner described in Example 7, showed a 77% reduction in fibrinogen adsorption. When coated on polyethylene ribbon in accordance with Example 8, it showed a 98% reduction in the activation of blood platelets.

By proceeding in an analogous manner using quinuclidine in place of pyridine an analogous compound was obtained in which a quinuclidinium group replaces the pyridinium group of the compound shown above. This compound, when coated on polyethylene tubing in accordance with Example 7 showed a reduction in fibrinogen adsorption of 31%.

By proceeding in an analagous manner using triphenylphosphine instead of pyridine and 6-bromohexan-1-ol instead of bromoethanol, a compound was isolated in 1% yield with a triphenylphosphinyl group in place of the pyridine and a hexyl spacer between the ions. This compound when coated on polyethylene tubing in accordance with Example 7 showed a reduction in fibrinogen adsorption of 28%, and when coated onto polyethylene ribbon in accordance with Example 8, but from a solution at 0.004 mmoles/ml, showed a reduction in the activation of platelets of 66%.

$^1$H-nmr (300 MHz, CDCl$_3$/CD$_3$OD), 0.88 (9H, m), 1.25–1.70 (64H, m), 3.27 (4H, s), 3.29 (4H, t), 3.56 (2H, m), 3.66 (2H, d), 3.81 (2H, d), 7.70–7.80 (15H, m)

$^{31}$P-nmr (121 MHz, CDCl$_3$/CD$_3$OD), –0.99 (1P,s), 25.01 (1P,s)

Example 5

1,3-dihexadecyloxy-2-(hydroxymethyl{[(hydroxyphosphinyl)oxy]-N,N,N,trimethyl hexanaminium hydroxide, inner salt}) 2-methylpropane

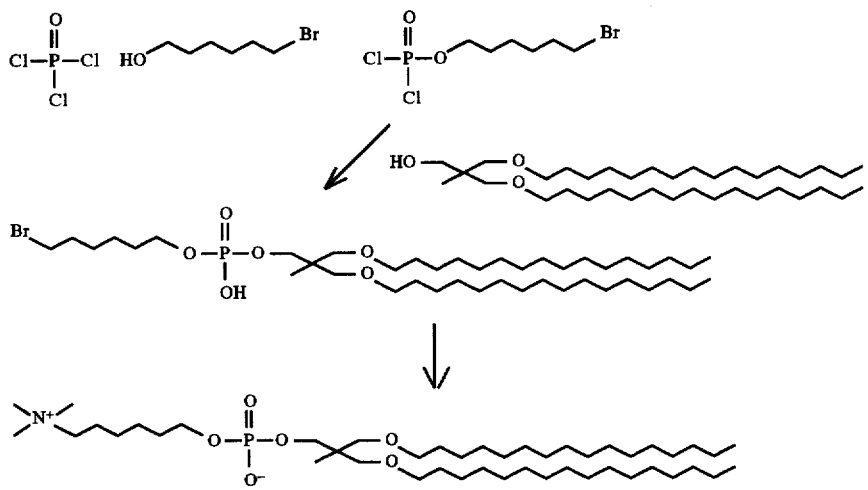

6-Bromohexan-1-ol (5.90 g, 32.61 mmol) in dry dichloromethane (30 ml) was added dropwise to phosphorus oxychloride (5.00 g, 32.61 mmol) in dry dichloromethane (30 ml). Nitrogen was bubbled through the reaction mixture for 4 hours. The solvent was removed by rotary evaporation to yield crude 6-bromohexyl-1-dichlorophosphate (9.70 g, 32.56 mmol), yield 100%.

$^1$H-nmr (200 MHz, CDCl$_3$), 1.48 (4H, m), 1.85 (4H, m), 3.41 (2H, t), 4.31, 4.38 (2H, dt).

Crude 6-(bromohexyl)-1-dichlorophosphate (1.05 g, 3.52 mmol) in dry ether (30 ml) was added to Compound A (1.00 g, 1.76 mmol) in dry ether (30 ml) with triethylamine (0.356 g, 3.52 mmol) stirred at room temperature under a nitrogen atmosphere. The reaction was stirred at room temperature for 12 hours. Triethylamine (0.356 g, 3.52 mmol) and water (1 ml) were added to the reaction mixture which was then refluxed for 3 hours. After cooling the aqueous layer was extracted with ether (5 ml×3). The combined ethereal layers were dried (sodium sulphate) and the solvent removed by rotary evaporation to yield a solid which was dried under reduced pressure. The solid was dissolved in dry chloroform (40 ml) and trimethylamine (1.50 g, 25.42 mmol) in acetonitrile (20 ml) was added and the reaction was stirred at 80° C. under a nitrogen atmosphere in a sealed vessel for 48 hours. After cooling the solvents were removed by rotary evaporation and the residue was purified by column chromatography eluted using chloroform:methanol:25% aqueous ammonia (690:270:64). Fractions containing the product were evaporated to dryness to give 1,3-dihexdecyloxy-2-(hydroxymethyl {[(hydroxyphosphinyl)oxy]N,N,N, trimethyl hexanaminium hydroxide, inner salt}) 2-methylpropane (231mg, 0.29 mmol) 17% yield.

$^1$H-nmr (300 MHz, CDCl$_3$), 0.88 (6H, t), 0.94 (3H, s), 1.26 (52H, m), 1.52 (8H, m), 1.64 (2H, m), 1.82 (2H, m), 3.26 (4H, s), 3.31 (9H, s), 3.34 (4H, t), 3.57 (2H, m), 3.72 (2H, d), 3.91 (2H, m).

$^{13}$C-nmr (50 MHz, CDCl$_3$), 14.1, 17.3, 22.1, 22.7, 24.5, 25.1, 26.2, 29.5, 31.9, 40.6, 53.1, 64.3, 66.1, 68.0, 71.6, 73.0.

Mass Spectrum: (FAB +ve ion m-nitrobenzyl alcohol matrix) M+1=791.

The compound thus obtained, when coated on polyethylene tubing in accordance with Example 7, showed a 92% reduction in fibrinogen adsorption and when coated on polyethylene ribbon, in accordance with Example 8, showed an 89% reduction in the activation of blood platelets.

Analogous compounds in which the length of the chain between the quaternary ammonium and phosphate moieties is varied were obtained by using a compound of formula HO(CH$_2$)$_n$Br in place of 6-bromohexan-1-ol, where n=3,5, 8,9,10,11 and 12. Analogues where n=4 or 16 where prepared by treatment of Compound B (described in example 9) with the relevant compound of formula HO(CH$_2$)$_n$Br, followed by treatment with trimethylamine and purification in an analagous manner to that described above. The reduction in fibrinogen adsorption and platelet activation on polyethylene tubing treated in accordance with Example 7 with these compounds is shown below together with the values of phospholipase digestion:

| n | % red'n fibrinogen | % red'n activ.pltls | % rxn pho'lipase C | % rxn pho'lipase D |
|---|---|---|---|---|
| 2 | 94 | 100 | 0 | 100 |
| 3 | 80 |  | 0 | 100 |
| 4 | 95 | 92 | 0 | 100 |
| 5 | 100 | 94* | 0 | 100 |
| 6 | 91 | 89* | 0 | 95 |
| 8 | 95 |  | 0 | 90 |
| 9 | 77 |  | 0 | 50 |
| 10 | 90 |  | 0 | 25 |
| 11 | 63 |  | 0 | 20 |
| 12 | 65 |  | 0 |  |
| 16 | 9 |  | 0 | 10 |

*Coated from a solution at 0.004 mmole/ml

Example 6

1,3 dihexadecyloxy-2-(hydroxymethyl) {[(hydroxy phosphinyl)oxy]-N,N,N, trimethyl alkanolaminium, inner salt}) 2-methyl propane.

6.1

Triethylamine (0.281 g, 2.77 mmol) and (2-chloroethyl)-phosphoric dichloride (0.503 g, 2.77 mmol) were added to Compound A (1.50 g, 2.64 mmol) in dry dichloromethane (40 ml). The reaction was stirred under a nitrogen atmosphere at room temperature for 48 hours. Triethylamine (0.281 g, 2.77 mmol) and water (3 ml) were added to the reaction mixture which was stirred at room temperature for a further 12 hours. The aqueous layer was removed and washed with dichloromethane (5 ml×3). The combined organic layers were dried (sodium sulphate) and the solvents removed by rotary evaporation to yield solid which was dried under reduced pressure. The solid was dissolved in dry chloroform (40 ml) and trimethylamine (1.50 g, 25.42 mmol) in acetonitrile (20 ml) was added. The reaction was stirred at 80° C. under a nitrogen atmosphere in a sealed vessel for 48 hours. After cooling the solvents were removed by rotary evaporation and the residue was purified by column chromatography eluting with chloroform:methanol:water (65:25:4). Fractions containing the product were evaporated to dryness to give 1,3 dihexadecyloxy-2-(hydroxymethyl) {[(hydroxy phosphinyl)oxy]-N,N,N, trimethyl ethanolaminium, inner salt}) 2-methyl propane (0.340 g, 0.474 mmol) 18% yield.

$^1$H-nmr (300 MHz, CDCl$_3$), 0.88 (6H, t), 0.96 (3H, s), 1.26 (52H, m), 1.53 (4H, m), 1.96 (2H, m), 3.11 (9H, s), 3.23 (4H, s), 3.38 (4H, t), 3.56 (2H, m), 3.11 (9H, s), 3.23 (4H, s), 3.38 (4H, t), 3.56 (2H, m), 3.74 (2H, m).

$^{13}$C-nmr (50 MHz, CDCl$_3$), 14.3, 17.3, 20.3, 22.8, 26.5, 29.7, 29.9, 32.0, 41.2, 53.1, 63.9, 67.4, 71.7, 72.9.

Mass Spectrum: (FAB +ve ion m-nitrobenzyl alcohol matrix) M+1=719.

The product thus obtained, when coated on polyethylene tubing in accordance with Example 7 showed a 20% reduction in fibrinogen adsorption and when coated on polyethylene ribbon in accordance with Example 8 showed a 58% reduction in the activation of blood platelets.

6.2

In an analagous manner, (3-chloropropyl)phosphonic dichloride was reacted with compound A and subsequently treated with trimethylamine to give 1,3-dihexadecyloxy-2-(hydroxymethyl){[(hydroxyphosphinyl)oxy]-N,N,N-trimethyl-propanolaminimium, inner salt}) 2-methyl propane in 29% yield.

$^1$H-nmr (300 MHz, CDCl$_3$/CD$_3$OD), 0.88 (6H, t), 0.94 (3H, s), 1.25 (52H, m), 1.51 (4H, m), 1.68 (2H, m), 2.03 (2H,m), 3.20 (9H, s), 3.26 (4H, s), 3.36 (4H, t), 3.54 (2H, m), 3.72 (2H, d)

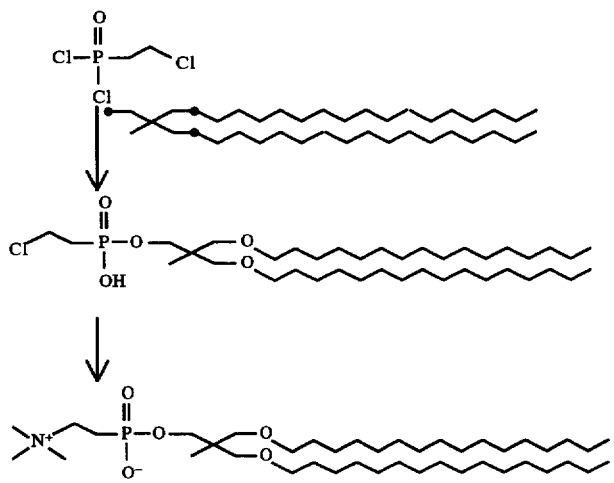

(3-Chloropropyl)phosphonic dichloride was prepared by converting chloropropyldibutyl phosphonate to chloropropyl phosphonic acid with subsequent transformation to the acid chloride using the methods described by B. Helferich and U. Curtius in *Liebigs Ann. Chem. Bd.*, 655, 59 (1962)

This compound when coated on polyethylene tubing in accordance with Example 7 showed a reduction in fibrinogen adsorption of 89%, and when coated onto polyethylene ribbon in accordance with Example 8, but from a solution at 0.004 mmoles/ml, showed a reduction in the activation of platelets of 100%. When incubated with phospholipase C or D, no significant hydrolysis was observed.

Example 7

Coating onto narrow bore polyethylene tubing

A piece of polyethylene tubing (1.6×300 mm) was washed with ethanol (passed through a 2 μm filter, 400 μl at 60° C.) for one minute. After decanting the ethanol a solution of the compound prepared in Example 4 (10.85 mg/ml, 13.3 μmol/ml) in ethanol (0.30 ml) was placed in the tube at 60° C. After leaving for one minute the solution was removed and the tubing dried under nitrogen.

By proceeding in an analogous manner samples were coated with compounds prepared in other Examples.

Example 8

Coating onto polyethylene ribbon

Polyethylene ribbon strips (102×25.5 mm) were washed with ethanol at 20° C. These strips were attached to a piece of PVC tubing (10 mm×60 mm) which was mechanically lowered (25 mm sec$^{-1}$) into a bath containing the compound prepared in Example 4 (10.85 mg/ml, 13.30 μmoles/ml, in ethanol (12.9 ml)) at 65° C., left for one minute and then removed at a speed of 4 mm/sec. The samples were dried in a laminar flow tent.

By proceeding in an analogous manner samples were coated with compounds prepared in other Examples.

Example 9

1,3-Dihexadecyloxy-2(hydroxymethyl){[(hydroxyphosphinyl)oxy]-N,N,N, trialkylethanium hydroxide, inner salt} 2-methyl propane 9.1

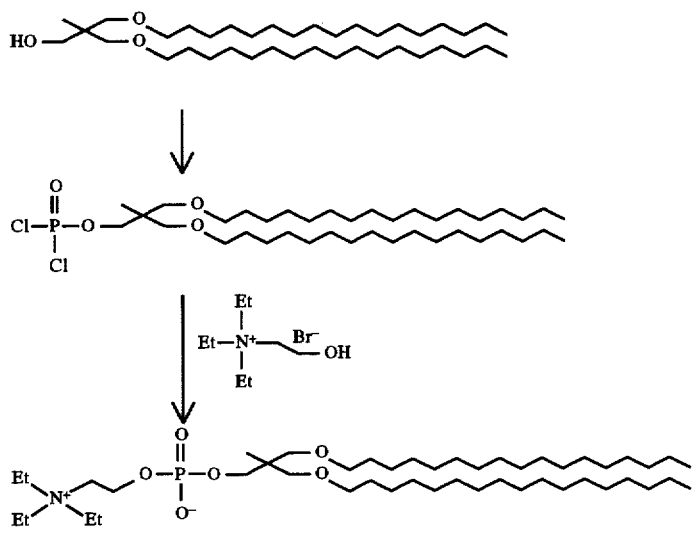

A solution of 1,3-dihexadecyloxy-2-(hydroxymethyl)-2-methyl propane (1 g, 1.75 mmole) in dry dichloromethane (15 ml) was added to phosphorus oxychloride (0.27 g, 1.75 mmole). A stream of nitrogen was passed through the stirred mixture for 16 hours. Further phosphorus oxychloride (0.54 g, 3.50 mmole) was added and the nitrogen flow maintained for a further 40 hours. The solvents were evaporated under pressure to give the crude dichlorophosphate (compound B).

Hydroxyethyltriethylammonium bromide (0.180 g, 1.23 mmole) and triethylamine (0.125 g, 1.23 mmole) in acetonitrile (25 ml) was added to the crude dichlorophosphate (0.84 g, 1.23 mmole). The mixture was heated at 50° C. for 16 hours. On cooling, water (1.33 ml, 74 mmole) and triethylamine (0.125 g, 1.23 mmole) were added and the mixture refluxed for two hours. The solvent was removed by evaporation and the residue azeotroped with benzene, before chromatographing on silica gel (80 g), eluting with chloroform:methanol (5:2) to chloroform:methanol:aqueous ammonia (690:270:64). Fractions containing product were combined, evaporated and dried under vacuum to give 1,3-dihexadecyloxy-2(hydroxymethyl)-{[(hydroxyphosphinyl)oxy]-N,N,N triethylethanium hydroxide, inner salt}2-methyl propane, 14 mg, 0.02 mmole, 2% yield.

$^1$H-nmr (200 MHz, CDCl$_3$), 0.90 (9H, m), 1.05–1.70 (65H, m), 3.26 (4H, s), 3.35 (4H, t), 3.53 (4H, m), 3.70 (4H, m), 4.30 (2H, m), Hydroxyethyltriethylammonium bromide was obtained as follows:

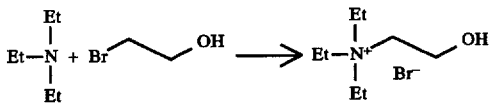

Bromoethanol (distilled, 2 g, 16 mmole) and triethylamine (1.62 g, 16 mmole) were heated in dichloromethane (30 ml) at 40° C. for 16 hours. After cooling the precipitate was filtered and dried over phosphorus pentoxide to yield hydroxyethyltriethylammonium bromide as a white powder, 1.47 g, 6.5 mmole, 41% yield.

$^1$H-nmr (200 MHz, D$_2$O), 1.62 (9H, m), 3.40 (8H, m), 4.00 (2H, s).

9.2

By proceeding in an analagous manner using hexyldimethylamine instead of triethylamine, and 2-(1-hydroxyethyl) tosylate instead of bromoethanol, a compound was isolated in 2% yield with a hexyldimethylamino group in place of the triethylammonium group. This compound when coated on polyethylene tubing in accordance with Example 7, but from a solution at 0.004 mmoles/ml, and showed a reduction in fibrinogen adsorption of 86%

$^1$H-nmr (200 MHz, CDCl$_3$/CD$_3$OD), 0.88–0.95 (12H, m), 1.25 (58H, m), 1.51 (4H, m), 1.65 (2H,m), 3.15 (6H, s), 3.20 (4H,s), 3.27 (6H,m), 3.60 (2H, m), 3.70 (2H, m), 4.23 (2H, m)

Example 10
1,1-Bis(hydroxymethyl)1-(methyloxy (trimethylammonium)phosphate, inner salt) ethane

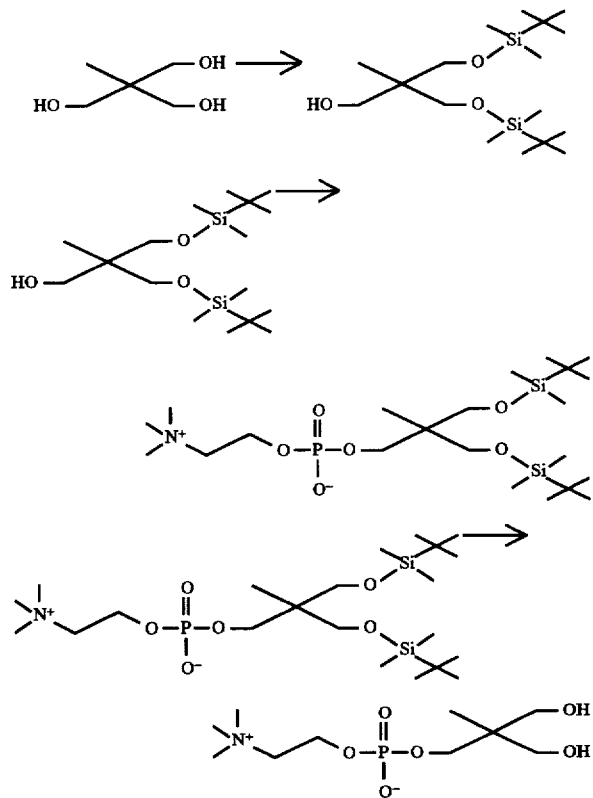

t-Butyldimethylsilyl chloride (5.27 g, 35 mmol) in acetone (50 ml) was added to tris(hydroxymethyl) ethane (4.21 g, 35 mmole) and triethylamine (3.56 g, 35 mmole) in dry acetone (200 ml). The reaction mixture was stirred at room temperature for two hours. The mixture was filtered and the solvent removed by rotary evaporation. The residue was dissolved in chloroform (100 ml) and washed 5 with water (100 ml×2), 0.1n hydrochloric acid (100 ml) and brine (100 ml). The organic layer was dried (sodium sulphate) and the solvent removed by rotary evaporation. The residue was purified by column chromatography using solvent ranging from dichloromethane to dichloromethane:acetone (2:1). Fractions containing product were evaporated to dryness to give {1,1-bis (tert-butyl dimethylsiloxymethyl) (1-hydroxymethyl)}1-ethane (2.1 g, 6.03 mmole, 17% yield).

$^1$H-nmr (200 MHz, CDCl$_3$)), 0.10 (12H, s), 0.85 (3H, s), 0.91 (18H s), 3.62 (6H, m), 4.90 (1H, s).

Triethylamine (0.61 g, 6.03 mmole) and bromoethyldichlorophosphate (1.46 g, 6.03 mmole) were added to {1,1-bis(tert-butyldimethylsiloxymethyl)(1-hydroxymethyl)}1-ethane (2.1 g, 6.03 mmole) in dry ether (30 ml) stirred under nitrogen at room temperature. The reaction was stirred at room temperature for 16 hours. Triethylamine (0.16 g, 6.03 mmole) and water (1 ml) were added and the reaction stirred at room temperature for three hours. The aqueous layer was extracted with ether (1 ml×3). The combined ethereal layers were dried (sodium sulphate) and the solvent removed by rotary evaporation to yield a gum which was dried under vacuum. The gum was dissolved in dry acetonitrile (20 ml) and trimethylamine (1.50, 25.42 mmole) in dry acetonitrile (20 ml) was added and the reaction was stirred at 80° C. under a nitrogen atmosphere in a sealed vessel for 48 hours. After cooling the solvents were removed by rotary evaporation and the residue was purified by column chromatography eluting with chloroform:methanol:25% aqueous ammonia (690:270:64). Fractions containing the product were evaporated to dryness to give 1,1-bis(tert-butyl dimethylsiloxymethyl)1-(methyloxy (trimethylammoniumethyl) phosphate, inner salt) ethane (0.240 g, 0.481 mmole, 8% yield).

$^1$H-nmr (200 MHz, CDCl$_3$)–0.02 (12H, s), 0.81 (21H, s), 3.32 (9H, s), 3.39 (4H, s), 3.61 (2H, m), 3.72 (2H, m), 4.22 (2H, m).

$^{13}$C-NMR (50 MHz, CDCl$_3$)–5.5, 16.3, 18.2, 25.8, 41.9, 54.2, 59.0, 64.5, 68.3.

1N Tetrabutyl ammonium fluoride (1.44 ml, 1.44 mmole) was added to 1,1-bis(tert-butyl dimethylsiloxymethyl)1-(methyloxy(trimethylammoniumethyl)phosphate, inner salt) ethane (0.24 g, 0.481 mmole) dissolved in dichloromethane (20 ml) and methanol (5 ml). The reaction mixture was stirred at room temperature for 16 hours. The solvents were removed by rotary evaporation and the residue was partitioned between dichloromethane (20 ml×4) and a solution of water (15 ml) and hydrobromic acid in acetic acid (5 ml). The aqueous layer was collected and the solvent removed by rotary evaporation and azeotroped with benzene (20 ml×3) before drying under vacuum. The resultant solid was extracted with ethanol (5 ml×5). The organic layer was filtered and the solvent removed by rotary evaporation and the residue was dried under high vacuum to give 1,1-bis (hydroxymethyl)1-(methyloxy(trimethylammonium) phosphate, inner salt) ethane.

$^1$H-nmr (200 MHz, D$_2$O), 0.88 (3H, s), 3.15 (9H, s), 3.51 (4H, s), 3.66 (2H, m), 3.74 (2H, m), 4.29 (2H, m).

Example 11
1,3-Dihexadecyloxy-2(hydroxymethyl) {[(hydroxyphosphinyl)amino]-N, N, N, trimethylethaninium hydroxide, inner salt}2-methyl propane

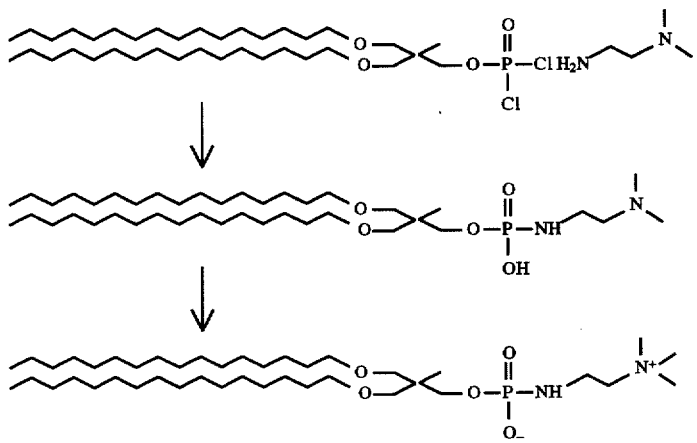

Compound B (0.604 g, 0.88 mmole) in a mixture of dry dichloromethane (10 ml) and acetonitrile (10 ml) was incubated with N,N-dimethylethylamine (78 mg, 0.88 mmole) and triethylamine (89 mg, 0.88 mmole) under nitrogen at 50° C. for 16 hours. Further triethylamine (89 mg, 0.88 mmole) and water (1 ml) were added and the temperature maintained for two hours. The solvents were removed by evaporation and the crude intermediate was added to a previously prepared mixture of potassium carbonate (1.39 g) and 18-crown-6 (2.2 g) in dry benzene (60 ml) which had been stirred for 20 minutes. Iodomethane (1 ml) was added and the mixture stirred at room temperature fo 16 hours. The solvent was removed under vacuum and the residue was triturated twice with acetone before drying, dissolving in chloroform and filtering to remove inorganic residues.

The chloroform solution was evaporated to give a crude product which was chromatographed on silica gel (25 g), eluting with chloroform to chloroform:methanol:aqueous ammonia (25%), (690:270:64). Fractions were assayed by tlc and those containing product were combined and evaporated to give the title compound, 89 mg, 0.11 mmole, 13% yield.

$^1$H-nmr (300 MHz, CDCl$_3$/CD$_3$OD), 0.88 (6H, t), 0.95 (3H, s), 1.25 (52H, m), 1.51 (4H, m), 3.28 (13H, m), 3.36 (4H, t), 3.50–3.99 (6H, m)

This compound when coated on polyethylene tubing in accordance with Example 7 showed a reduction in fibrinogen adsorption of 64%, and when coated onto polyethylene ribbon in accordance with Example 8, but from a solution at 0.004 mmoles/ml, showed a reduction in the activation of platelets of 99%. When incubated with phospholipase D approximately 50% of the compound was hydrolysed when compared to standard phospholipids. No hydrolysis was observed with phospholipase C.

Example 12

1,3-dihexadecyloxy-2-(hydroxymethyl {2'-[trimethylammonium]malonate}half ester

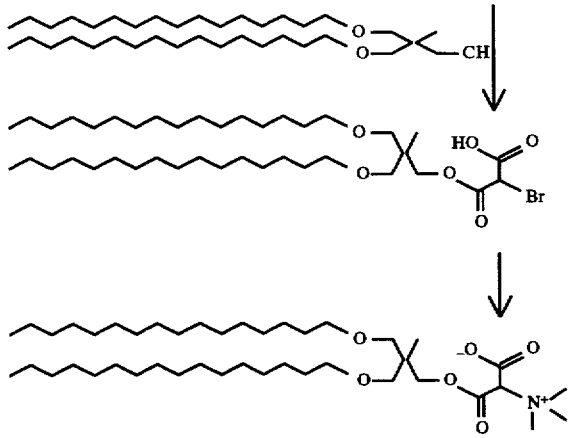

Malonyl chloride (7.05 g, 50 mmole) in carbon tetrachloride (30 ml) was added N-bromosuccinimide (10.7 g, mmole), followed by hydrobromic acid (40%, 4 drops). The mixture was heated at 70 for ten minutes and at 85° C. for ninety minutes. After cooling, the solvent was evaporate to give a dark residue which was dissolved in dry ether (ca 100 ml), filtered and re-evaporated. The residue was distilled under reduced pressure to give an initial fraction containing 2-bromomalonyl chloride (1H-nmr (singlet, 5.52)) 3 g, 14 mmole, 27% yield. A second fraction was also isolated.

Compound A (500 mg, 0.88 mmole) was dissolved in dry ether (15 ml) and successively treated with 2-bromomalonyl chloride (483 mg, 2.20 mmole) and triethylamine (223 mg, 2.20 mmole). The mixture was stirred at room temperature for sixteen hours, filtered to remove the solid and evaporated to a coloured gum. This was redissolved in chloroform (50 ml) and stirred with an equal volume of saturated sodium bicarbonate solution for one hour. The layers were separated and the organic layer dried over sodium sulphate, evaporated to dryness and redissolved in a mixture (1:1) of dichloromethane and acetonitrile (60 ml). This was treated with trimethylamine (2.6 g) and heated in a sealed vessel at 70° C. for 16 hours. The resulting solid was removed, and the liquors were evaporated to dryness, redissolved in chloroform (30 ml) and washed with water (2×30 ml), before the organic layer was dried over sodium sulphate, evaporated and the residue purified by silica chromatography, eluting with chloroform to chloroform:methanol:ammonia (25%) (690:270:64). Fractions containing the product were combined, evaporated, azeotroped with benzene (×2) and dried under vacuum for two hours to give the title compound, 45 mg, 0.06 mmole, 7% yield.

$^1$H-nmr (300 MHz, CDCl$_3$/CD$_3$OD), 0.88 (6H, t), 0.95 (3H, s), 1.25 (52H, m), 1.51 (4H, m), 3.10–3.45 (19H, m), 4.70 (1H, d)

This compound when coated on polyethylene tubing in accordance with Example 7 showed a reduction in fibrinogen adsorption of 71%, and when coated onto polyethylene ribbon in accordance with Example 8, but from a solution at 0.004 mmoles/ml, showed a reduction in the activation of platelets of 86%.

Example 13

1,3-dihexadecyloxy-2-(hydroxymethyl{[(hydroxyphosphinyl)oxy]N-methylpyridinyl-2-hydroxide, inner salt}) 2- methyl propane 1.73 mmole) in dried acetonitrile (5 ml) and ether (5 ml) was added dropwise a solution of compound B (1.18 g, 1.73 mmole) in dry acetonitrile (10 ml). The mixture was heated to 40° C. for 16 hours. Water (1.87 g) and triethylamine (0.17 g, 1.73 mmole) were added and the mixture heated at 40° C. for 2 hours. The solvents were removed by evaporation, the residue was azeotroped with benzene and dried under vacuum to give crude product.

The crude product was subjected to successive silica gel columns, eluting initially with chloroform to chloroform:methanol:water (65:25:4) and latterly with chloroform:methanol: aqueoua ammonia (25%) (690:270:64). Fractions containing pure product were combined, evaporated to dryness and dried under vacuum to give the title compound, 242 mg, 0.33 mmole, 19% yield from compound B.

$^1$H-nmr (300 MHz, CDCl$_3$/CD$_3$OD), 0.89 (6H, t), 0.97 (3H, s), 1.30 (52H, m), 1.55 (4H, m), 3.27 (4H, s), 3.34 (4H, t), 3.88 (2H, d), 4.45 (3H, s), 6.20 (1H,d), 6.28 (1H,d), 6.88 (1H, s), 7.80 (1H, m)

$^{13}$C-nmr(50 MHz, CDCl$_3$/CD$_3$OD), 14.0, 17.0, 22.6, 26.1, 29.3, 29.6, 31.8, 40.6, 40.9, 48.6, 69.5, 71.6, 72.7, 127.9, 135.7, 137.8, 138.2, 154.1

Mass Spectrum: (FAB +ve ion m-nitrobenzylalcohol matrix) M+1=740

This compound when coated on polyethylene tubing in accordance with Example 7 showed a reduction in fibrinogen adsorption of 71%, and when coated onto polyethylene ribbon in accordance with Example 8, but from a solution at

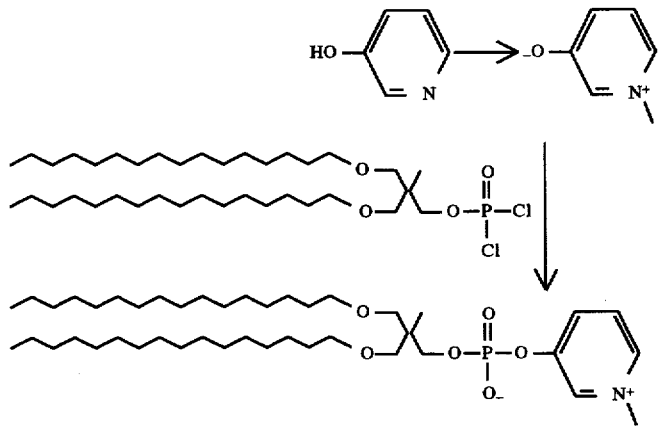

3-Hydroxypyridine (0.5 g, 5.2 mmole) and methyltosylate (1.47 g, 7.89 mmole) were dissolved in dry acetonitrile (20 ml) and heated to 50° C. for 16 hours. The resulting precipitate was filtered through a sintered glass funnel and dried over phosphorus pentoxide under vacuum for 48 hours. The product was dissolved in dry acetonitrile (20 ml) and swirled with Amberlite 401 ion-exchange resin (5 g, preactivated and washed by successive treatment with sodium hydroxide (1M, 1l), water (1l) and acetone (1l)) for four hours. The mixture was filtered and the filtrate evaporated and dried under reduced pressure to give N-methyl-2-oxy pyridinium inner salt. To N-methyl-2-oxy-pyridinium inner salt (0.28 g, 2.59 mmole) and triethylamine (0.17 g, 0.004 mmoles/ml, showed a reduction in the activation of platelets of 94%. When incubated with phospholipase C, no hydrolysis was observed, but with phospholipase D, almost complete (95%) hydrolysis was seen when compared to natural phosphatidyl choline.

Example 14

1,3-dihexadecyloxy-2-(hydroxymethyl-{[(hydroxyphosphinyl)oxy]-S,S-dimethylethylsulphonium hydroxide, inner salt}) 2-methyl propane

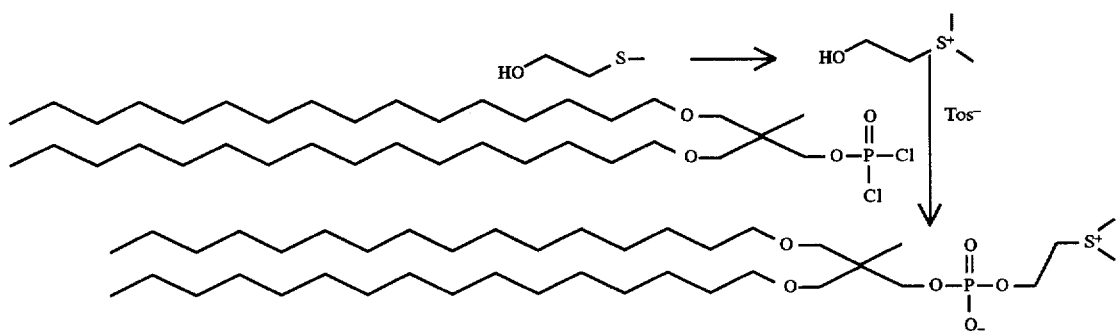

Methylthioethanol (0.5 g, 5.42 mmole) and methyl tosylate (2.0 g, 10.85 mmole) were dissolved in dichloromethane (20 ml) and stirred at 30° C. for 16 hours. The reaction mixture was evaporated and the resulting solid triturated with petroleum ether, filtered and dried under vacuum over phosphorus pentoxide for four hours to give dimethylthioethanol tosylate salt (1.28 g, 4.59 mmole, 85% yield). This compound (0.49 g, 1.75 mmole) was mixed with triethylamine (0.18 g, 1.75 mmole) in dry acetonitrile (10 ml) and added to a solution of compound B (1.2 g, 1.75 mmole) in dry ether (20 ml) and stirred at 50° C. for 16 hours. The mixture was cooled, and evaporated to dryness. The solution was treated with a mixture of chloroform:methanol:aqueous ammonia (690:270:64) and purified by two successive solutions from silica gel chromatography columns, eluting with chloroform:methanol:aqueous ammonia (690:270:64). Fractions containing pure product were combined, evaporated to dryness, azeotroped with benzene, and the solid triturated with hexane and acetone before drying under vacuum to give the title compound, 40 mg, 0.054 mmole, 3% yield.

$^1$H-nmr (300 MHz, CDCl$_3$/CD$_3$OD), 0.88 (6H, t), 0.95 (3H, s), 1.25 (52H, m), 1.49 (4H, m), 3.04 (6H,s), 3.28 (4H, s), 3.35 (4H, t), 3.58 (2H, m), 3.71 (2H, d), 4.26 (2H,m)

$^{13}$C-nmr(50 MHz, CDCl$_3$/CD$_3$OD), 14.0, 17.0, 22.9, 26.5, 27.0, 30.0, 30.3, 33.0, 41.2, 46.4, 59.4, 69.0, 72.3, 73.5

This compound when coated on polyethylene tubing in accordance with Example 7 showed a reduction in fibrinogen adsorption of 31%, and when coated onto polyethylene ribbon in accordance with Example 8, but from a solution at 0.004 mmoles/ml, showed a reduction in the activation of platelets of 77%.

Example 15

1,2-dihexadecyloxy-2-(hydroxymethyl){2'-carboxy-4' [trimethylammonium]butanoate}

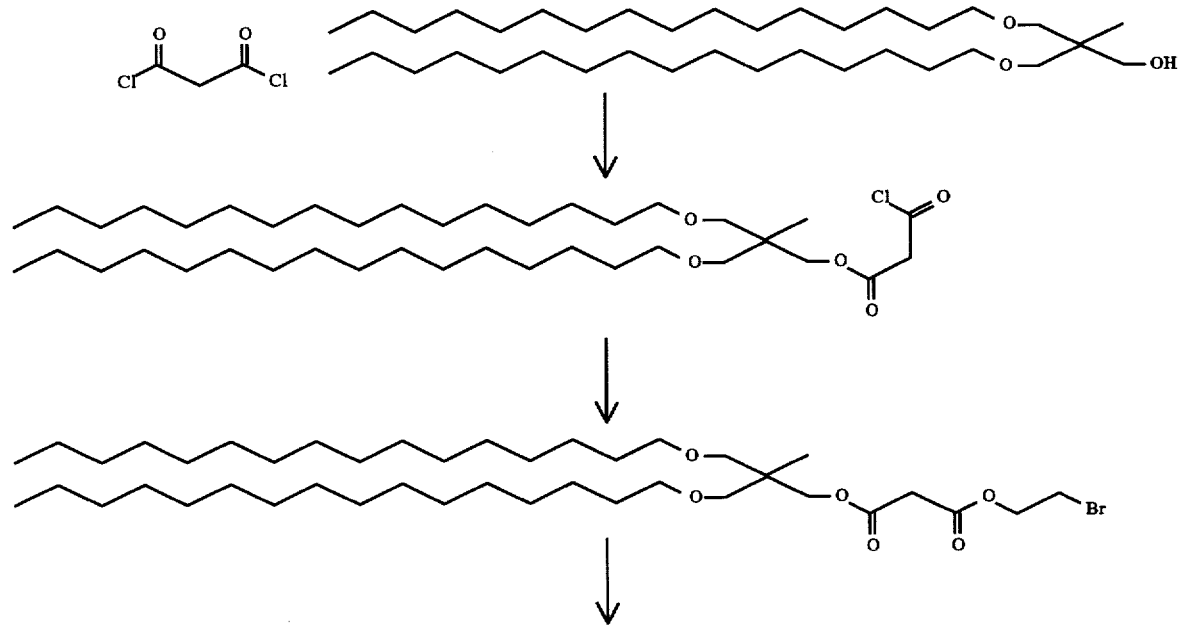

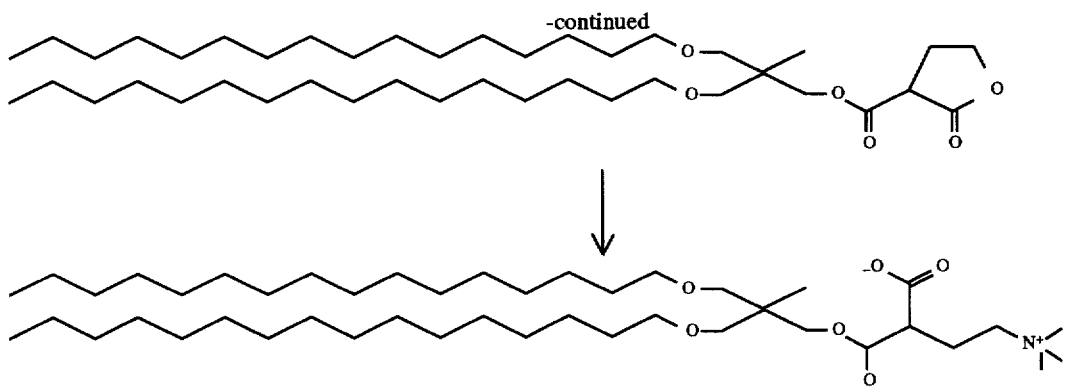

To compound A (500 mg, 0.88 mmole) in dry ether (20 ml) was added triethylamine (89 mg, 0.88 mmole) and malonyl chloride (620 mg, 4.4 mmole). The mixture was stirred at ambient temperature for two hours, after which the precipitate was removed by filtration, was washed with further dry ether and dichloromethane, and the combined filtrate and washings evaporated to dryness. The residue was dried under high vacuum at 50 C. for ninety minutes to give the acid chloride ester.

$^1$H-nmr (200 MHz, CDCl$_3$), 0.88 (6H,t) 0.95 (3H,s), 1.25–1.70 (56H,m), 3.25 (4H, s), 3.30–3.40 (6H,m), 4.10 (2H,s).

This was dissolved in dry dichloromethane (10 ml) and successively treated with triethylamine (89 mg, 0.88 mmole) and bromoethanol (110 mg, 0.88 mmole) before stirring at room temperature for 6 hours. The mixture was extracted with saturated sodium bicarbonate solution (3×100 ml) after diluting with dichloromethane (90 ml). The organic layer was dried over sodium sulphate and evaporated to give a crude product, 0.6 g, which was purified by chromotography on silica gel (25 g), eluting with dichloromethane. Fraction containing product were isolated by evaporation to give the bromoethyl ester, contaminated with co-eluting his ester of compound A, 0.21 g.

$^1$H-nmr (200 MHz, CDCl$_3$), 0.88 (6H,t), 0.95 (3H,t), 0.95 (3H, s), 1.25–1.75 (56H,m), 3.25 (4H,s), 3.30–3.45 (6H,m), 3.50 (2H,y), 4.10 (2H,s), 4.45 (2H,t).

The mixture was treated, as a solution in dry dichloromethane (20 ml), with lithium diisopropylamide (1.5M solution in cyclohexane, 0.14 ml, 0.216 mmole) at –40° C. The mixture was allowed to warm to ambient temperature whilst stirring over a period of 90 minutes. The solvents were evaporated and the residue shown to contain lactone by nmr.

$^1$H-nmr (200 MHx, CDCl$_3$), 0.88 (6H,t), 0.95 (3H,t), 1.25–1.65 (56H,m), 2.65 (2H,m), 3.20–3.50 (12H,m), 4.00 (1M,m), 4.40 (2H,t).

The residue was dissolved in dichloromethane (3 ml) and filtered to remove the solids, which were washed with further dichloromethane (3 ml). The combined foiltrated and washings were treated with trimethylamine (6.4 g, 108 mmole) in dry acetonitrile (60 ml) and the mixture heated in a sealed flask at 80 C. for 16 hours. The mixture was filtered and the filtrate concentrated before purifying on a silica column, eluting with chloroform/methanol (4:1). Fractions containing the product were concentrated to give a whit solid containing the product.

$^1$H-nmr (200 MHz, CDCl$_3$/CD$_3$OD), 0.88 (6H,t), 0.95 (3H,s), 1.25–1.53 (58Hm), 3.04 (9H,s), 3.25–3.60 (12H,m), 4.40–4.60 (1H,m).

We claim:

1. A biocompatible polymer comprising a group of the formula (I)

in which the groups —B are the same or different, and each is —OH$_2$— or —C(=O)—, R$^1$ is hydrogen or an alkyl group of 1 to 12 carbon atoms and Z is a zwitterionic group, in which the groups of the formula (I) are covalently bound in the polymer through groups B.

2. A material according to claim 1 in which the anionic group of the zwitterionic group is closer to the central carbon atom of the group of the formula I than the anionic group.

3. A polymer according to claim 1 which is a polyester or a polyurethane.

4. A polymer according to claim 1 formed from a monomer containing a group of the formula (I) and an ethylenically unsaturated polymerisable group which is attached to B.

5. A method of improving the biocompatibility of a surface which comprises providing a surface having groups of formula (I)

in which the groups —B are the same or different, and each is —CH$_2$— or —C(=O)—, R$^1$ is hydrogen or an alkyl group of 1 to 12 carbon atoms and Z is a zwitterionic group, in which the groups of the formula (I) are covalently bound in the polymer through groups —B.

6. A method according to claim 5 in which a performed surface is treated to introduce the groups of the formula 1 onto the surface.

7. A method according to claim 5 in which the surface is created by shaping a polymer obtained by the polymerisation or copolymerisation of compounds containing the group of formula (I)

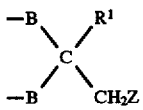

in which the groups —B— are the same or different, and each is —CH$_2$— or —C(=O)—, $R^1$ is hydrogen or an alklyl group of 1 to 12 carbon atomsn and Z is a zwitterionic group.

8. A blood contacting device having a blood contacting surface which comprises a biocompatible polymer as defined in claim 1.

9. A tear film contacting device having a surface which contacts tear film, in which the surface comprises a biocompatible polymer as defined in claim 1.

10. A biocompatible polymer according to claim 1 in which the groups B are the same as one another.

11. A biocompatible polymer according to claim 10 in which the groups B are joined to identical groups.

12. A biocompatible polymer according to claim 1 in which each of the groups B are attached to oxygen atoms by ether linkages.

13. A biocompatible polymer according to claim 1 in which the anionic moiety of the zwitterionic group is selected from phosphate, sulphonate, phosphate ester and carboxylate groups.

14. A biocompatible polymer according to claim 1 in which the cationic moiety of the zwitterionic group is selected from quaternary ammonium groups, phosphonium groups and sulphonium groups.

15. The biocompatible polymer of claim 1, wherein B is —CH$_2$—.

16. The biocompatible polymer of claim 1, wherein $R^1$ has 1 to 4 carbon atoms.

17. The biocompatible polymer of claim 12, wherein the attaching is by ether linkages.

18. The biocompatible polymer of claim 13, wherein the anionic moiety is selected from the group consisting of a phosphate ester group and a carboxylate groups.

19. The biocompatible polymer of claim 14, wherein the cationic moiety is a quaternary ammonium group.

20. A biocompatible polymer formed by polmerising monomers having formula (I') groups with comonomers, wherein formula (I') is as follows:

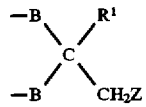

in which the groups —B are $R^2$—YB in which $R^2$ is hydrogen and the Y groups are each —O— or —NH— and B is —CH$_2$—;

$R^1$ is hydrogen or an alkyl group of 1 to 12 carbon atoms; and Z is a zwitterionic group, in which the groups of the formula (I) are covalently bound in the polymer through groups B.

21. The polymer of claim 4, wherein the ethylenically unsaturated polymerisable group is selected from the group consisting of an (alk)acrylate group, an (alk)acrylamide group, a vinyl group and a styrene group.

* * * * *